United States Patent [19]

Mardorf et al.

[11] Patent Number: 4,465,475

[45] Date of Patent: Aug. 14, 1984

[54] INJECTOR FOR MEDICAL USES

[75] Inventors: Robert Mardorf; Sigfried Hessberg, both of Melsungen, Fed. Rep. of Germany

[73] Assignee: Intermedicat GmbH, Emmenbrücke, Switzerland

[21] Appl. No.: 447,968

[22] Filed: Dec. 8, 1982

[30] Foreign Application Priority Data

Dec. 21, 1981 [DE] Fed. Rep. of Germany ....... 3150623

[51] Int. Cl.³ ............................................... A61M 5/20
[52] U.S. Cl. .............................. 604/155; 128/DIG. 1
[58] Field of Search ............... 604/154, 155, 224, 131; 128/DIG. 2, DIG. 1

[56] References Cited

U.S. PATENT DOCUMENTS 2,734,504  2/1956  Crescas et al. ...................... 604/155
3,415,419  12/1968  Jewitt et al. .................. 128/DIG. 1
4,191,187  3/1980  Wright ........................... 128/DIG. 1

Primary Examiner—Stephen C. Pellegrino
Attorney, Agent, or Firm—Kenyon & Kenyon

[57] ABSTRACT

An injector for squeezing liquid from a medical syringe is disclosed. On a housing (10), a first holder is (11) fastened. A first end of a syringe cylinder is joined to the first holder (11). The syringe piston (15) is joined to a second holder (13). The second holder (13) is fastened to a slide (12) which is displaceable relative to the housing (10). The drive of the slide (12) is effected by way of a pipe (26) and a ball gear (27, 28) on a spindle (28). The end of the spindle (28) is connected with the slide (12) through a free-wheeling mechanism. The spindle (28) can be rotated by hand with a rotary button (30). When the free-wheeling mechanism is released, the slide (12) can be pulled linearly into a desired position. The ball gear drive mechanism (27, 28) ensures that when the motor is turned on, the slide (12) is driven at once without first requiring an engagement of a tooth system or a screwthread.

9 Claims, 3 Drawing Figures

INJECTOR FOR MEDICAL USES

FIELD OF INVENTION

This invention relates to an injector for medical uses. More particularly this invention relates to an injector for medical uses comprising a housing containing a spindle drive, a first holder mounted on the housing for attachment of one part of a syringe, a slide movable linearly relative to the housing and driven by a motor via the spindle drive, which slide has a second holder mounted thereon for attachment to the other part of the syringe, and a release which upon actuation interrupts the transmission of force from the motor for moving the slide.

BACKGROUND OF THE INVENTION

Injectors of the type to which the present invention is directed (such injectors sometimes being referred to as "pressure infusion devices") are used for carrying out long-term infusions of a liquid into a patient. They are suitable for actuating a syringe slowly and continuously, so that the contents of the syringe are supplied to a patient connected to the outlet of the syringe in a uniform manner over an extended period of time (e.g., 24 hours). The injectors typically, therefore, supply minute quantities of liquid at a rate, e.g., of 0.06 to 6 ml/h with a high degree of uniformity of the rate of supply over the time of operation and with the velocity deviation being generally limited to about 1% maximum.

Injectors are known wherein the syringe is squeezed by means of a rack-and-pinion drive mechanism driven by a synchronous motor with reversing gear. The front end of the syringe cylinder is retained in a holder. A second holder, connected with the piston rod of the syringe, is slowly moved in the direction of the first holder.

More recent injectors are equipped with a spindle drive instead of a rack. This spindle drive is driven by a step motor or by a direct current motor via a transmission. The spindle drive can be disengaged through a release device to enable presetting the piston rod by hand. This, however, involves the following problems: When using the injector, the syringe is first filled from a bottle containing medication using a cannula. Then the cannula is removed, and an empty tube is taken from a sterile package and connected to the syringe outlet. For reasons of sterility, cleanliness, and economy, it is desirable to fill the tube exactly up to its free end before a cannula or catheter is connected to it. In known injectors, this filling of the tube is effected by advancing the slide with the release device actuated until the liquid just reaches the front end of the tube. When actuation of the release device is terminated, either an engagement with the graduations or screw-thread of the spindle or rack occurs or the engagement does not occur. If after actuation of the release device has terminated, engagement of the spindle or rack occurs, a jerking motion forward or backward may occur at the slide which results in air entering the tube or liquid being discharged from the tube. On the other hand, if engagement does not occur when actuation of the release device is terminated, the engagement will occur later with a certain delay, namely after the spindle or rack has moved sufficiently for engagement to be possible. As an example, with a rate of feed of 1 ml/h, a piston path of 80 mm in 50 hours, and a speed at the output end of 1.6 mm/h, and assuming that the spindle pitch is 1 mm, it may take as long as 40 minutes before engagement occurs. During this time, injection does not take place even though the patient is hooked up to the injector. This may lead to thrombus formation and finally embolism. For this reason, a forcible engagement is usually provided for.

If the engagement is brought about forcibly after the tube has been connected to the patient, there are two undesirable and medically risky effects. The engagement leads either to a brief reversal of the direction of flow as a result of which blood is sucked from the patient causing danger of thrombus formation and embolism, or else there is a concentrated surge of medication to the patient.

Another disadvantage of the known injectors is that when the release device is actuated under load, the initial tensions are relieved suddenly.

OBJECT OF THE INVENTION

It is therefore an object of the present invention to provide an injector for medical uses whose slide is freely movable when the release device is actuated.

It is another object of the present invention to provide an injector for medical uses wherein it is possible to establish the transmission of force to the drive in every position of the slide continuously ("steplessly") and without a ratchet effect.

It is further object of the present invention to provide an injector for medical uses which permits exact fine adjustments prior to the beginning of the infusion process.

These and other objects will become apparent from the following description and claims in conjunction with the drawings.

SUMMARY OF THE INVENTION

To solve the problems associated with the prior art, the present invention comprises a medical injector spindle drive having a ball gear comprising a nut disposed on the spindle with the nut being in engagement with the thread of the spindle through balls. The release device, in accordance with the invention, is a coupling device which couples either the spindle or the nut non-rotationally with the injector's slide in at least one direction of rotation.

The present invention may be generally summarized as an injector for medical uses including an elongated housing containing a spindle drive having a threaded spindle, a first holder mounted on said housing for attachment to one part of a syringe, a slide movably mounted to said housing for linear motion relative to the direction of elongation of said housing, a motor for driving said slide via said spindle drive, a second holder mounted on said slide for attachment to the other part of the syringe, and means for interrupting the transmission of force from said motor, the improvement comprising:

said spindle drive includes a ball gear comprising a nut surrounding said threaded spindle wherein said nut is in engagement with the threads of said spindle through balls; and coupling means for non-rotationally coupling said spindle with said slide in at least one direction of rotation of said spindle.

In an alternate embodiment of the present invention, the coupling means non-rotationally couples the nut with the slide in at least one direction of rotation of the nut.

BRIEF DESCRIPTION OF THE DRAWINGS

In the drawing forming part hereof.

DESCRIPTION OF THE PREFERRED EMBODIMENTS

In order to afford a more complete understanding of the present invention and an appreciation of its advantages, a description of the preferred embodiments is presented below.

A ball gear drive is a spindle drive which is non-self-locking. This means that by rotation of the nut relative to the spindle there is obtained not only a longitudinal relative movement between nut and spindle, but also as a result of the linear displacement of the spindle relative to the nut a rotation of these two parts relative to each other. Such planetary ball gears are known, for example, from DE-OS No. 14 25 787 the disclosure of which is incorporated herein by reference. They comprise a nut which has threads matching the threads of the spindle. However, the threads of the nut and spindle do not engage one in the other, but form helical channels in which balls are provided. Upon a relative movement between spindle and nut, these balls travel in the interior of the nut, and when they have reached the end of the nut, they are brought back through axial return channels to the opposite end of the nut. Due to the extremely low friction of the ball gear, the result is that with the nut rotating, the spindle is moved linearly relative to the nut. On the other hand, the spindle can also be displaced linearly with respect to the nut when the nut is non-rotationally fixed in a stationary position because the spindle will rotate freely with respect to the nut. This is, therefore, a non-self-locking spindle drive.

Through the use of the ball gear, the slide of the injector of the present invention can be moved linearly to any desired position if the spindle can rotate freely. If thereafter, the spindle is connected with the slide by a coupling device, the transmission of force between a motor and the slide is established immediately without an engagement in a graduation or thread of the spindle being required. The slide is connected to a second holder and the piston rod of the syringe is fastened to the second holder. Thus, the slide can be adjusted exactly for the respective syringe. It is also possible, by manually moving the slide, to fill a tube connected to the syringe from the syringe with the spindle rotating freely. When the liquid has arrived at the front end of the tube, the spindle is coupled to the slide so that the further movement of the slide occurs via the spindle drive from the motor. This permits an exact fine adjustment of the syringe at the beginning of the injection process.

Figure 1:
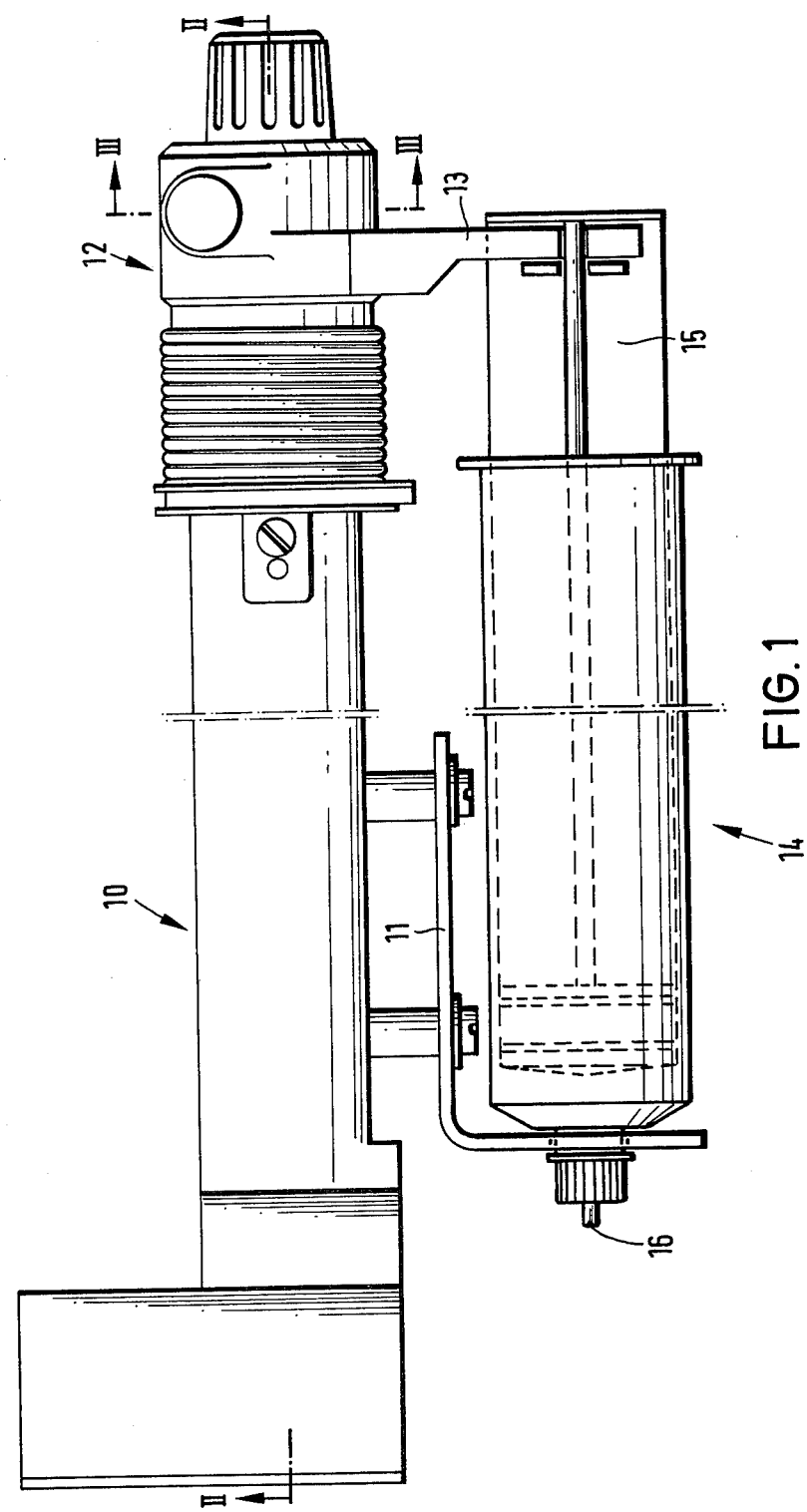
FIG. 1 is a side view of an injector for medical use in accordance with one embodiment of the present invention.
Figure 2:
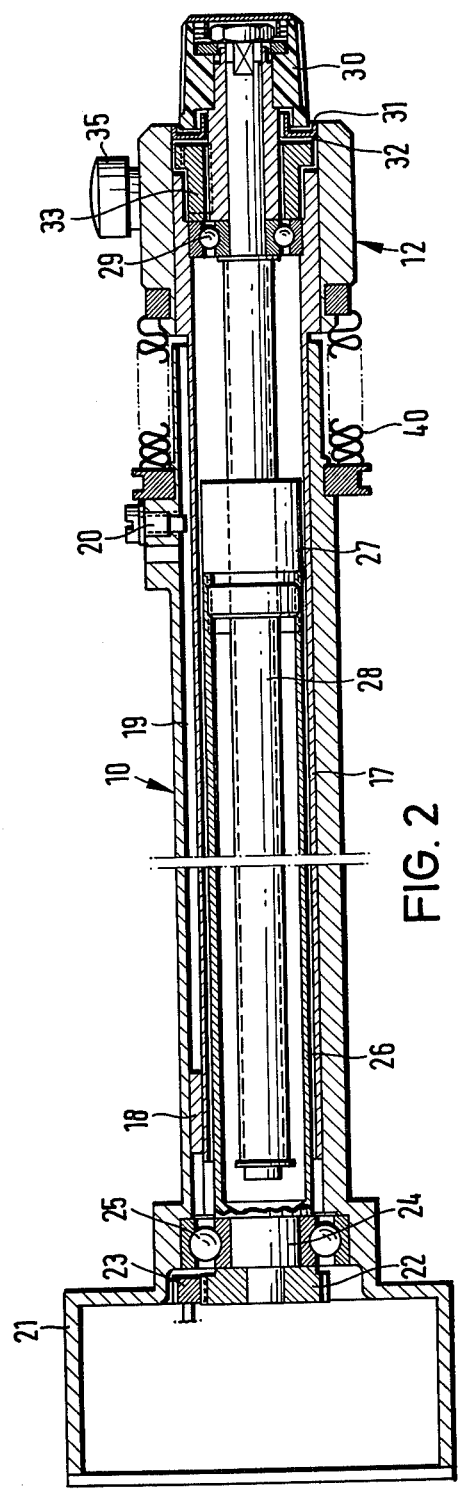
FIG. 2 is a longitudinal sectional view of an embodiment of the present invention taken along line II—II of FIG. 1.

According to a preferred embodiment of the invention and with reference to FIG. 2, the spindle 28 which is coupled with the slide 12 or alternately with the nut 27, is connected with a rotary button or knob 30. The coupling device is a freewheeling mechanism which in the coupled state permits the rotation of the spindle 28 or alternately the nut 27 by the rotary button 30 only in the direction which corresponds to a mutual approach of the second holder 13 towards first holder 11. (See FIG. 1).

As a result, the spindle or the nut can be rotated by hand with the rotary button, so that by turning the rotary button a fine displacement of the two holders toward each other takes place. During this fine displacement, a tube connected to the syringe outlet may be filled with liquid exactly up to its front end. The liquid cannot be sucked back into the tube because reverse rotation of the button is prevented by the freewheeling mechanism. Therefore, the invention substantially prevents contamination from being sucked from the outside air into the tube. The fine displacement is also possible under load with the motor running.

In principle, either the spindle 28 or the nut 27 may be connected with the slide 12 via the coupling device. What is important is that only one of these two parts is driven by the motor and that the other part is connected to the slide and thus can be connected non-rotationally with the slide via the coupling device.

According to a preferred embodiment of the invention and with reference to FIG. 2, the spindle drive comprises a pipe 26 driven by the motor and firmly connected with the nut 27, in which pipe 26 the spindle 28 is arranged. This has the advantage of a favorable design because the rotary button 30 can be firmly connected directly with the end of the spindle. Expediently, the slide 12 is guided non-rotationally by a sleeve 17 which surrounds the pipe 26 which is located in the pipe socket of the housing 10. The entire spindle drive is lodged encapsulated in the pipe socket and is thus protected against harmful external influences.

Figure 3:
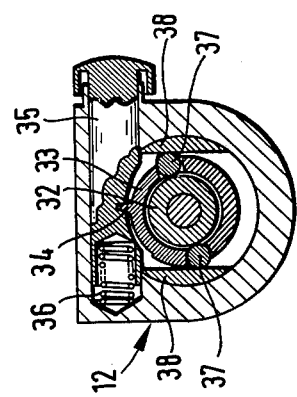
FIG. 3 is a transverse section of an embodiment of the present invention taken along line III—III of FIG. 1.

According to a preferred embodiment of the invention and with reference to FIG. 3, the freewheeling mechanism comprises a ring 33 which contains needles 37 and can be rotated by a release button 35. The needles 37 engage against the outside of a shaft section or shaft collar 32 connected with the spindle 28 and are guided between tangential wall portions 38 of the slide 12. Such a needle freewheeling mechanism, as it is known in principle also in bicycles, has the advantage that it immediately prevents backward rotation, while permitting unhindered forward rotation. In case of backward rotation, the needles 37 become wedged between the shaft section 32 and the tangential wall portions 38 thereby preventing backward rotation.

In the following, an embodiment of the invention is explained more specifically with reference to the drawings.

The injector of one embodiment of the present invention illustrated in FIG. 1 comprises an elongated tubular-like housing 10 to the underside of which an L-shaped first holder 11 is secured. The free leg of first holder 11 is bent downward. In housing 10, a slide 12 is guided. The slide 12 protrudes from the free end of the housing and has joined to it a downwardly projecting second holder 13. The vertical leg of the first holder 11 is provided with a lateral recess into which is inserted the neck of the cylinder of a syringe 14. From the rear end of the cylinder a piston rod 15 protrudes, the end of which is inserted into a recess in the second holder 13. It will be appreciated that if the second holder 13 is moved in the direction of the first holder 11, the contents of the syringe is squeezed out of the syringe outlet 16. A sterile flexible tube (not shown) would be connected to the syringe outlet 16.

Referring to FIG. 2, a sleeve 17 is firmly connected with slide 12 and is guided for longitudinal displacement in the tubular housing 10. At the end of sleeve 17 remote from slide 12, sleeve 17 has a radially projecting shoulder 18 which engages and slides in a longitudinal groove 19 positioned on the inside of housing 10. When the slide 12 is fully extended, radially projecting shoulder 18 of sleeve 17 abuts against a stop screw 20 which penetrates through the wall of housing 10 into longitudinal groove 19. The shoulder 18 also serves as a mechanism to prevent rotation of slide 12 relative to housing 10 by the engagement of shoulder 18 in groove 19. The drive-side (left) end 21 of housing 10 serves for the attachment of a motor (not shown). In this end 21, a gear 22 is mounted, which is driven by the motor through a pinion 23. The gear 22 is connected with a pipe 26 through a shaft piece 24 mounted in ball bearings 25. Pipe 26 is coaxially positioned inside the tubular housing 10 and inside the sleeve 17. Nut 27 of the ball gear is located at the free end of pipe 26. This nut 27 cooperates with the spindle 28, which extends from the side of slide 12 coaxially into the interior of pipe 26. The interaction of nut 27 with spindle 28, which has hereinbefore been discussed, is not illustrated in detail in the drawing. This design can be seen, for example, in DE-OS No. 14 25 787 the disclosure of which is incorporated herein by reference.

The end of spindle 28 is mounted in slide 12 by ball bearings 29. A rotary button 30 is fixed at the end of spindle 28. Rotary button 30 is displaceable together with slide 12. Spindle 28 can be rotated manually by rotary button 30. At slide 12, the spindle end is secured against axial displacements.

Referring to FIG. 2 and FIG. 3, in the interior of slide 12, a shaft piece 32 connected with the spindle end is surrounded by a switching ring 33 which can be rotated within limits. Referring to FIG. 3, the switching ring 33 has a radially projecting nose 34 which protrudes into a transverse notch in a pressure pin 35. The pressure pin 35 extends in slide 12 above the shaft piece 32 and crosswise thereto. It is guided in a blind hole and is biased outwardly with respect to the side by a spring 36.

The switching ring 33 forms a cage for two needles 37. These needles engage against the outside of the circumferential wall of the shaft piece or shaft collar 32. On the other hand, the needles 37 engage against the tangential inner face of pressure pieces or tangential wall sections 38. The pressure pieces 38 form together with the shaft piece 32 (seen in transverse section ) wedge-shaped channels for the balls or needles 37. This results in a freewheeling effect, because the shaft piece 32, which is connected with spindle 28, can freely rotate only counter-clockwise as viewed in FIG. 3. Upon clockwise rotation of the shaft piece 32, the needles 37 are wedged in at the pressure pieces 38 so that such a rotation is blocked immediately.

If the pressure pin 35 is pressed in counter to the action of spring 36, the switching ring 33 is swiveled counter-clockwise, so that the needles 37 are necessarily brought into their release position, thereby permitting rotation of the shaft piece 32 and therefore spindle 28 in both directions.

Between slide 12 and the end of housing 10 facing it, there is a bellows 40 which covers sleeve 17 of slide 12 and closes housing 10.

The injector is operated as follows: To insert a filled syringe, the slide 12 is pulled out of housing 10, starting from the position shown in FIG. 2. This is done by pushing pin 35 in. With the pin pushed in, if one pulls on slide 12 (to the right as seen in FIG. 2), sleeve 17 moves to the right in housing 10, while nut 27 is held in place by the motor which is still turned off. After slide 12 has been pulled out as far as the filled syringe requires, syringe 14 is inserted into the two holders 11, 13. Pin 35 is now let go. In this state, the rotary knob 30 can be rotated only in the direction which corresponds to a movement of the second holder 13 toward the first holder 11, not in the opposite direction. Knob 30 is rotated until the tube connected to the syringe outlet 16 has become filled with liquid from the syringe. Since spindle 28 takes support on the nut 27 which is still stationary (the motor has not yet been turned on), the gear clearance or play is also eliminated by tension in the working direction caused by actuation of rotary knob 30.

After the flexible tube has been connected to the patient, the motor can be turned on. Due to the absence of play, transport of liquid starts immediately even at lowest rates of infusion or injection.

It will be appreciated that when nut 27 is held in place by turning off the motor and when pin 35 is pushed in, the slide 12 may be displaced manually in both directions. The spindle 28 rotates in the nut 27 which is held in place. The slide, therefore can be adjusted to any desired position when pin 35 is depressed.

For reasons of clearer illustration in the drawing, the motor for the drive of pipe 26 and of nut 27 has been omitted. A limit switch which turns the motor off when slide 12 has reached its position of maximum retraction relative to housing 10, or if overload occurs, is also not shown. Likewise, means for manually turning the motor on and off are not shown as they are well known and may be readily provided by one skilled in the art.

Although preferred embodiments of the present invention have been described in detail, it is contemplated that modifications may be made by one skilled in the art within the spirit and scope of the invention.

What is claimed is:

1. In an injector for medical uses including an elongated housing containing a spindle drive having a threaded spindle, a first holder mounted on said housing for attachment to one part of a syringe, a slide movably mounted to said housing for linear motion relative to the direction of elongation of said housing, a motor for driving said slide via said spindle drive, a second holder mounted on said slide for attachment to the other part of the syringe, and means for interrupting the transmission of force from said motor, the improvement comprising:

said spindle drive includes a ball gear comprising a nut surrounding said threaded spindle wherein said nut is in engagement with the threads of said spindle through balls; and coupling means for non-rotationally coupling said spindle with said slide in at least one direction of rotation of said spindle.

2. An injector as recited in claim 1 further comprising:

a button connected to said spindle for manually rotating said spindle; and wherein said coupling means is a free-wheeling mechanism which in the coupled state permits the rotation of said spindle only in the rotational direction which corresponds to the direction of linear movement of said slide causing the mutual approach of said first and second holders.

3. An injector as recited in claim 2 wherein said spindle drive further comprises a pipe wherein said spindle is disposed within said pipe and said pipe has a first end connected to said motor and a second end firmly connected to said nut whereby said motor rotationally drives said pipe and thereby said nut.

4. An injector as recited in claim 3 further comprising:
a sleeve surrounding said pipe; wherein
said sleeve is movably mounted within said housing for linear motion therein;
said sleeve has one end firmly connected to said slide; and
means for preventing rotation of said sleeve with respect to said housing whereby said sleeve guides said slide in non-rotational linear motion with respect to said housing.

5. An injector as recited in claim 2 wherein said free-wheeling mechanism comprises:
a switching ring containing needles positioned within said slide and surrounding said spindle;
a shaft collar surrounding and fixed to said spindle at a position where said spindle penetrates said switching ring wherein said needles of said switching ring contact said collar and permit rotation of said switching ring about said collar from a first position to a second position;
tangential pressure pieces mounted within said slide external to and adjacent to said switching ring wherein said needles contact said pressure pieces when said switching ring is in said first position so that attempted rotation of said spindle in one direction results in said needles being wedged between said collar and said pressure pieces thereby preventing rotation of said spindle in said one direction and rotation of said spindle in the other direction is permitted;
a release button mechanism adjacent said switching ring including means for engaging said switching ring and for rotating said switching ring to said second position when said release button is operated wherein said needles are remote from said pressure pieces in said second position thereby permitting rotation of said spindle in both said one and other directions.

6. An injector as recited in claim 1 wherein said spindle drive further comprises a pipe wherein said spindle is disposed within said pipe and said pipe has a first end connected to said motor and a second end firmly connected to said nut whereby said motor rotationally drives said pipe and thereby said nut.

7. An injector as recited in claim 6 further comprising:
a sleeve surrounding said pipe; wherein
said sleeve is movably mounted within said housing for linear motion therein;
said sleeve has one end firmly connected to said slide; and
means for preventing rotation of said sleeve with respect to said housing whereby said sleeve guides said slide in non-rotational linear motion with respect to said housing.

8. In an injector for medical uses including an elongated housing containing a spindle drive having a threaded spindle, a first holder mounted on said housing for attachment to one part of a syringe, a slide movably mounted to said housing for linear motion relative to the direction of elongation of said housing, a motor for driving said slide via said spindle drive, a second holder mounted on said slide for attachment to the other part of the syringe, and means for interrupting the transmission of force from said motor, the improvement comprising:
said spindle drive includes a ball gear comprising a nut surrounding said threaded spindle wherein said nut is in engagement with the threads of said spindle through balls; and
coupling means for non-rotationally coupling said nut with said slide in at least one direction of rotation of said nut.

9. An injector as recited in claim 8 further comprising:
a button connected to said nut for manually rotating said nut; and wherein
said coupling means is a free-wheeling mechanism which in the coupled state permits the rotation of said nut only in the rotational direction which corresponds to the direction of linear movement of said slide causing the mutual approach of said first and second holders.

* * * * *